(12) United States Patent
Steiner et al.

(10) Patent No.: US 8,146,588 B2
(45) Date of Patent: Apr. 3, 2012

(54) UNIT DOSE CAPSULES AND DRY POWDER INHALER

(75) Inventors: Solomon S. Steiner, Mount Kisco, NY (US); Robert Feldstein, Yonkers, NY (US); Per B. Fog, Bedford Hills, NY (US); Trent A. Poole, South Amherst, MA (US)

(73) Assignee: MannKind Corporation, Valencia, CA (US)

( * ) Notice: Subject to any disclaimer, the term of this patent is extended or adjusted under 35 U.S.C. 154(b) by 1022 days.

(21) Appl. No.: 11/949,707

(22) Filed: Dec. 3, 2007

(65) Prior Publication Data

US 2008/0127970 A1 Jun. 5, 2008

Related U.S. Application Data

(62) Division of application No. 09/621,092, filed on Jul. 21, 2000, now Pat. No. 7,305,986.

(60) Provisional application No. 60/145,464, filed on Jul. 23, 1999, provisional application No. 60/206,123, filed on May 22, 2000.

(51) Int. Cl.
*A61M 15/00* (2006.01)
*A61M 15/06* (2006.01)
(52) U.S. Cl. ......... 128/203.15; 128/203.12; 128/203.13; 128/203.14; 128/203.21; 128/203.23
(58) Field of Classification Search ............ 128/200.14, 128/200.15, 200.16, 200.17, 200.21, 200.23, 128/203.12, 203.15, 203.21, 203.23, 200.24
See application file for complete search history.

(56) References Cited

U.S. PATENT DOCUMENTS

| 2,549,303 | A | | 4/1951 | Friden | |
|---|---|---|---|---|---|
| 3,622,053 | A | * | 11/1971 | Ryden | 222/402.11 |
| 3,669,113 | A | | 6/1972 | Altounyan et al. | |
| 3,823,816 | A | | 7/1974 | Controullis et al. | |
| 3,823,843 | A | | 7/1974 | Stephens et al. | |
| 4,040,536 | A | | 8/1977 | Schwartz | |
| 4,047,525 | A | | 9/1977 | Kulessa et al. | |
| 4,148,308 | A | | 4/1979 | Sayer | |
| 4,275,820 | A | | 6/1981 | LeBlond | |
| 4,300,546 | A | * | 11/1981 | Kruber | 128/200.16 |
| 4,456,007 | A | * | 6/1984 | Nakao et al. | 128/200.21 |
| 4,487,327 | A | | 12/1984 | Grayson | |
| 4,792,451 | A | | 12/1988 | Kim | |
| 4,991,605 | A | | 2/1991 | Keritsis | |
| 5,027,806 | A | | 7/1991 | Zoltan et al. | |
| 5,067,500 | A | | 11/1991 | Keritsis | |
| 5,152,284 | A | | 10/1992 | Valentini et al. | |
| 5,170,801 | A | | 12/1992 | Casper et al. | |
| 5,328,464 | A | | 7/1994 | Kriesel et al. | |
| 5,337,740 | A | * | 8/1994 | Armstrong et al. | 128/203.12 |
| 5,447,151 | A | * | 9/1995 | Bruna et al. | 128/203.15 |

(Continued)

FOREIGN PATENT DOCUMENTS

DE 3639836 A1 6/1988

(Continued)

*Primary Examiner* — Clinton T Ostrup
(74) *Attorney, Agent, or Firm* — K & L Gates LLP; Louis C. Cullman; Brian J. Novak

(57) ABSTRACT

Described are dry powder inhalers composing an intake section, a mixing section and a mouthpiece. The mixing section can accommodate a capsule having a top keying portion and containing a dry powder medicament. The top keying portion of the capsules may fit within complementary keying structures in inhaler mixing sections.

28 Claims, 10 Drawing Sheets

U.S. PATENT DOCUMENTS

| | | | |
|---|---|---|---|
| 5,476,093 A | 12/1995 | Lankinen | |
| 5,503,144 A * | 4/1996 | Bacon | 128/203.15 |
| 5,524,613 A | 6/1996 | Haber et al. | |
| 5,562,918 A | 10/1996 | Stimpson | |
| 5,568,884 A * | 10/1996 | Bruna | 222/189.09 |
| 5,632,971 A | 5/1997 | Yang | |
| 5,727,546 A | 3/1998 | Clarke et al. | |
| 5,752,505 A * | 5/1998 | Ohki et al. | 128/203.15 |
| 5,758,638 A | 6/1998 | Kreamer | |
| 5,797,391 A | 8/1998 | Cook et al. | |
| 5,896,855 A | 4/1999 | Hobbs et al. | |
| 5,904,139 A * | 5/1999 | Hauser | 128/200.23 |
| 6,109,261 A | 8/2000 | Clarke et al. | |
| 6,116,237 A | 9/2000 | Schultz et al. | |
| 6,158,431 A * | 12/2000 | Poole | 128/203.12 |
| 6,298,846 B1 * | 10/2001 | Ohki et al. | 128/203.15 |
| 6,606,992 B1 | 8/2003 | Schuler et al. | |
| 6,655,379 B2 | 12/2003 | Clark et al. | |
| 6,698,421 B2 * | 3/2004 | Attolini | 128/200.14 |
| 7,305,986 B1 | 12/2007 | Steiner et al. | |

FOREIGN PATENT DOCUMENTS

| | | |
|---|---|---|
| DE | 19519840 A1 | 12/1996 |
| EP | 0143524 | 5/1985 |
| EP | 0180543 | 5/1986 |
| EP | 0308637 A1 | 3/1989 |
| EP | 0388821 | 9/1990 |
| EP | 0581473 A1 | 2/1994 |
| EP | 0666085 A1 | 8/1995 |
| EP | 0844007 | 5/1998 |
| GB | 0716815 | 10/1954 |
| GB | 2072536 A | 10/1981 |
| GB | 2148841 A | 6/1985 |
| GB | 2253200 A | 9/1992 |
| GB | 2262452 | 6/1993 |
| JP | 10234827 A | 9/1998 |
| WO | 01/19524 | 12/1991 |
| WO | 94/19041 | 9/1994 |
| WO | 96/22802 A | 8/1996 |
| WO | 98/26827 A1 | 6/1998 |
| WO | 98/41255 A2 | 9/1998 |
| WO | 01/07107 | 2/2001 |
| WO | 01/66064 | 9/2001 |
| WO | 03/05547 | 7/2003 |

* cited by examiner

PISTON NORMALLY CLOSES
INTAKE PORT

2ND SPRING NOT SHOWN

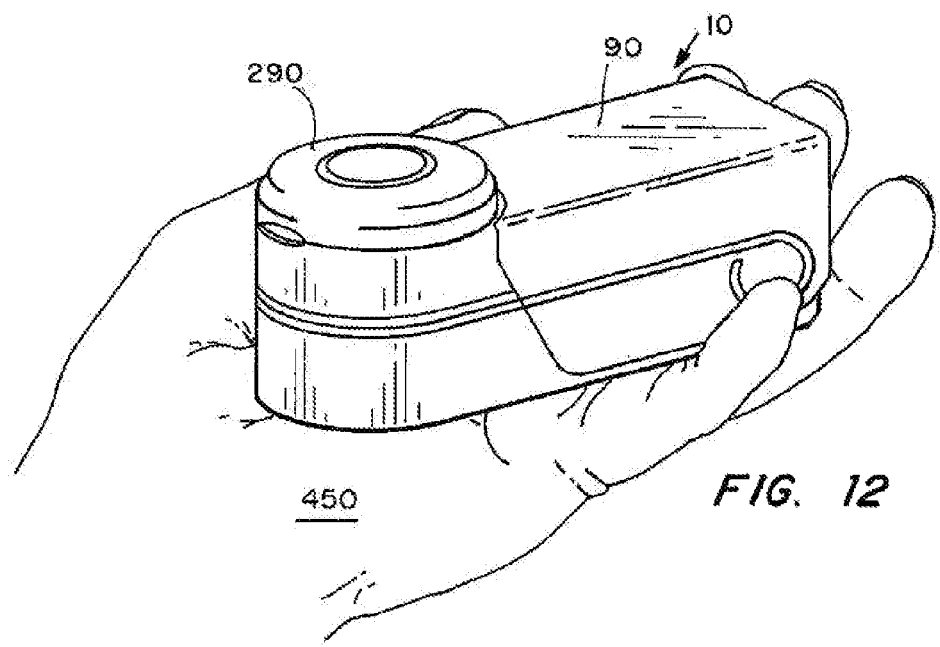
FIG. 12
FIG. 13
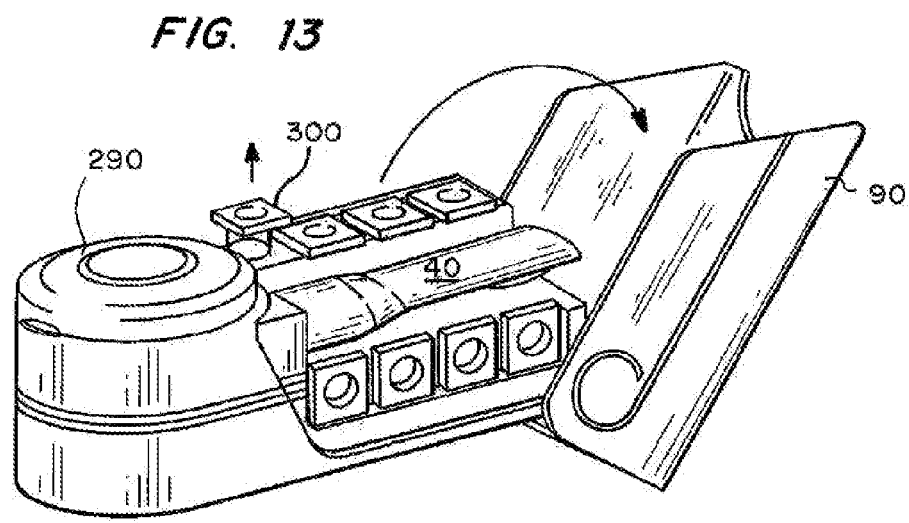

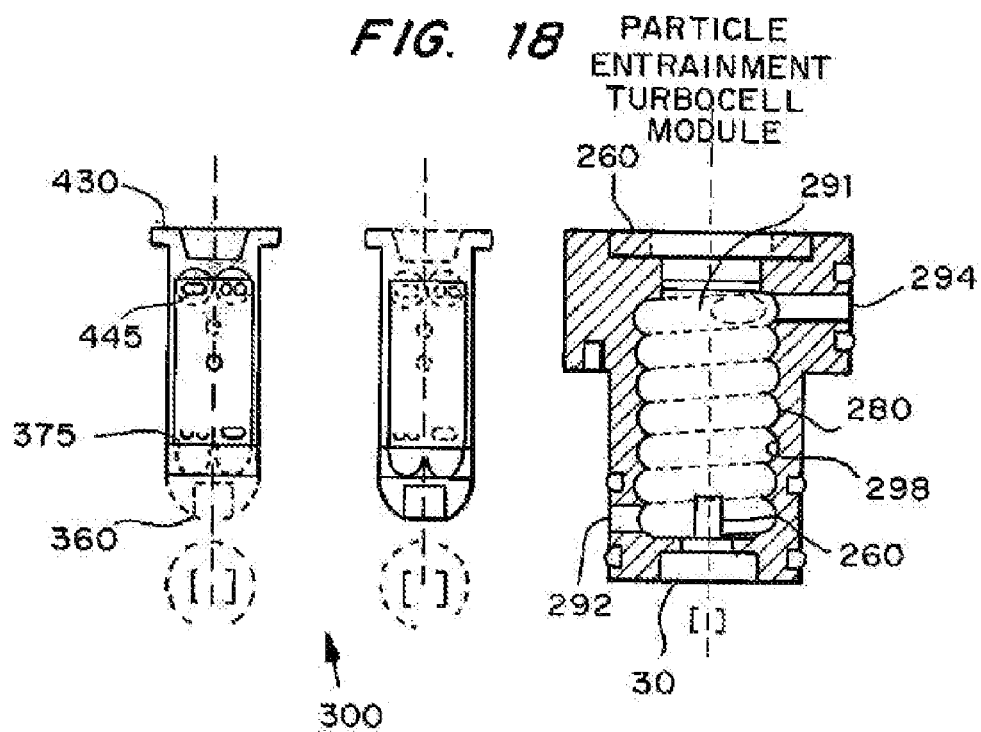
FIG. 18 PARTICLE ENTRAINMENT TURBOCELL MODULE
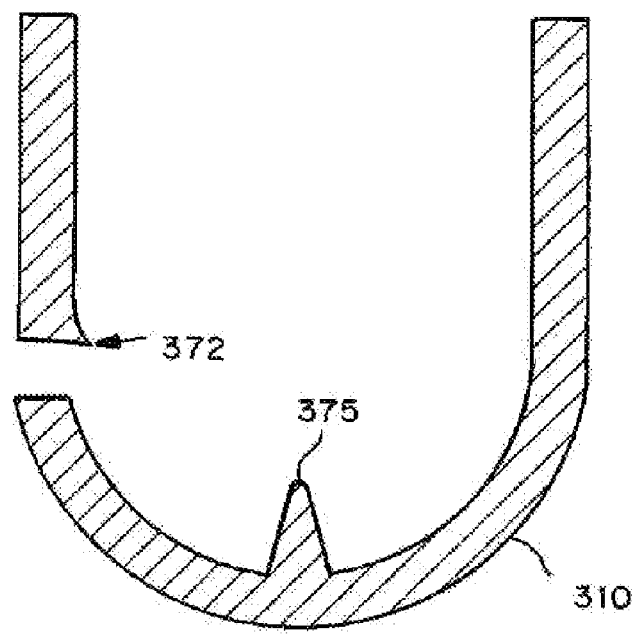
FIG. 19

UNIT DOSE CAPSULES AND DRY POWDER INHALER

CROSS REFERENCE TO RELATED APPLICATIONS

The present application is a divisional of U.S. patent application Ser. No. 09/621,092 filed on Jul. 21, 2000 which claims the benefit under 35 U.S.C. §119(e) of U.S. Provisional Patent Applications Nos. 60/145,464 filed Jul. 23, 1999 and 60/206,123 filed May 22, 2000, all of which are incorporated by reference herein in their entirety.

FIELD OF THE INVENTION

The present invention is in the field of inhalers.

BACKGROUND OF THE INVENTION

In the early 1970's it was found that certain medicines could be administered in dry-powder form directly to the lungs by inhalation through the mouth or inspiration through the nose. This process allows the medicine to bypass the digestive system, and may, in certain cases, allow smaller doses to be used to achieve the same results for orally ingested or injected medicines. In some cases, it provides a delivery technique that reduces side effects for medicines taken by other medicines.

Inhaler devices typically deliver their medicine in a liquid mist or a powder mist. The liquid mist is typically created by a chlorofluorocarbon propellant. However, with the ban on chlorofluorocarbons by the Montreal protocol, interest has turned to dry powder inhalers.

For a dry powder inhaler to work effectively, it must deliver fine particles of medicinal powder that do not agglomerate, and do not end up striking, and being absorbed by the patient's mouth or upper oropharyngeal region. Air flow must therefore not be too fast. Furthermore, it should not be difficult for a patient to load with medicine or to use with the proper technique. Current dry particle inhalers fail in one or more of these important criteria.

SUMMARY OF THE INVENTION

Described is a dry powder inhaler comprising an intake section; a mixing section, and a mouthpiece. The mouthpiece is connected by a swivel joint to the mixing section, and may swivel back onto the intake section and be enclosed by a cover. The intake chamber comprises a special piston with a tapered piston rod and spring, and one or more bleed-through orifices to modulate the flow of air through the device. The intake chamber further optionally comprises a feedback module to generate a tone indicating to the user when the proper rate of airflow has been achieved. The mixing section holds a capsule with holes containing a dry powder medicament, and the cover only can open when the mouthpiece is at a certain angle to the intake section. The mixing section further opens and closes the capsule when the intake section is at a certain angle to the mouthpiece. The mixing section is a Venturi chamber configured by protrusions or spirals to impart a cyclonic flow to air passing through the mixing chamber. The mouthpiece includes a tongue depressor, and a protrusion to contact the lips of the user to tell the user that the DPI is in the correct position. An optional storage section, with a cover, holds additional capsules. The cover for the mouthpiece, and the cover for the storage section may both be transparent magnifying lenses.

The capsules may be two-part capsules where each portion has apertures which correspond to apertures in the other half when each half is partially fitted to the other half, and fully fitted to the other half. All the apertures may be closed when the two halves are rotated around their longitudinal axes with respect to each other. Each capsule may have a unique key on each half that only fits with a particular inhaler.

Therefore it is an object of the invention to provide a dry particle inhaler that can fold into a compact form.

Therefore it is an object of the invention to provide a dry particle inhaler that can be loaded with medicament easily.

Therefore it is an object of the invention to provide a dry particle inhaler where the small writing on a capsule of medicament can be easily read.

Therefore it is an object of the invention to provide a dry particle inhaler where a capsule containing medicament can only be inserted when a person unfolds the inhaler for use.

Therefore it is an object of the invention to provide a dry particle inhaler where the air flow through the device is regulated.

Therefore it is an object of the invention to provide a dry particle inhaler to provide a means for indicating to the user when the air flow is at the correct rate.

Therefore it is an object of the invention to provide a dry particle inhaler where particles of drug are dispersed finely.

These and other objects of the invention will be readily apparent upon a reading of the present specification, claims and drawings.

BRIEF DESCRIPTION OF THE SEVERAL VIEWS OF THE DRAWINGS

FIGS. 12, 13, 14, and 15 follow each other in temporal sequence.

FIG. 12 is a perspective view of a specific embodiment of the dry particle inhaler showing a closed mouthpiece cover.

FIG. 13 is a perspective view of a specific embodiment of the dry particle inhaler showing an open mouthpiece cover.

FIG. 14 is a perspective view of a specific embodiment of the dry particle inhaler showing an open mouthpiece cover, an open mixing section cover, and a capsule about to be inserted into the mixing section.

FIG. 15 is a perspective view of a specific embodiment of the dry particle inhaler showing the mouthpiece extended for use.

FIG. 18 is a cutaway view of a capsule and a portion of the mixing section.

FIG. 19 is a cutaway view of half of a capsule, showing a cone in the interior and a secondary hole with a chamfered, or beveled, edge.

Figure 1:
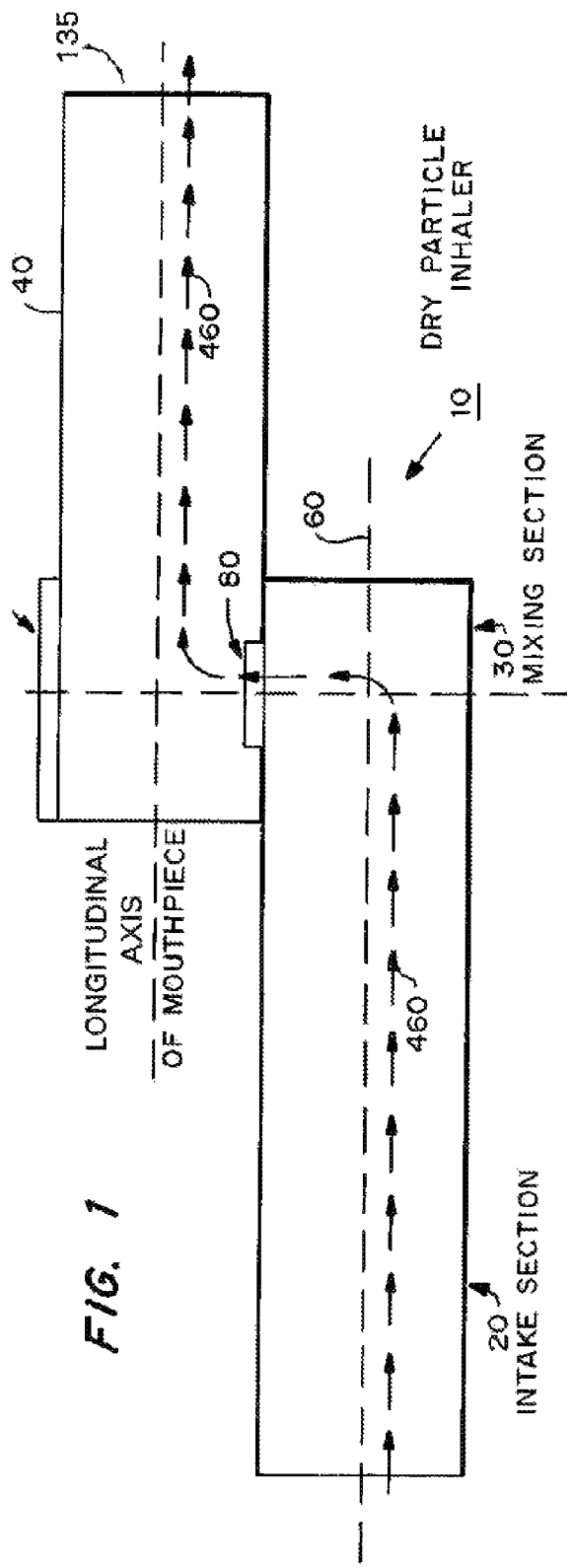
FIG. 1 is a schematic view of the dry particle inhaler described herein.

TABLE OF REFERENCE NUMBERS 10 dry powder inhaler device
20 intake section
30 mixing section
40 mouthpiece
50 air passage through dry powder inhaler device
60 longitudinal axis of intake section
70 longitudinal axis of mouthpiece section
80 swivel joint connecting mouthpiece and mixing section
90 cover for mouthpiece
100 protrusions on mouthpiece cover
110 depressions on dry particle inhaler cover to mate with protrusions on mouthpiece cover
120 tongue depressor on mouthpiece
130 protrusion on surface of mouthpiece to contact lips of device user
135 opening of mouthpiece to be fitted into user's mouth
140 intake port
150 flow regulator
160 bleed orifice
170 piston
180 piston head
190 piston rod
200 proximal portion of piston rod
210 distal portion of piston rod
220 spring
230 inner walls of intake section inner chamber
240 feedback module
250 mechanical fasteners in storage section
260 holder in mixing section for capsule
270 Venturi chamber
280 spiral shape or protrusions to impart cyclonic flow to air
290 cover for mixing chamber
291 interior of mixing section
292 air flow entrance to mixing section
294 air flow exit from mixing section
296 latch mechanism for mixing section cover
298 interior wall of mixing section
300 capsule
310 first tube
320 open end of first tube
330 closed end of first tube
340 long axis of first tube
350 protrusion on first tube
360 keying surface on first tube
370 secondary holes in first tube
372 chamfered edge of secondary hole
375 cone in interior of first tube
380 second tube
390 open end of second tube
400 closed end of second tube
410 long axis of second tube
420 protrusion on second tube
430 keying surface on second tube
440 secondary holes in second tube
445 cone in interior of second tube
450 hand of user
460 air flow direction
470 storage section
480 storage section cover

DETAILED DESCRIPTION OF THE INVENTION

FIG. 1 is a schematic drawing of the dry powder inhaler (10) described herein. It comprises an intake section (20), a mixing section (30) and a mouthpiece (40). An air passage (50) goes through the intake section (20), a mixing section (30) and a mouthpiece (40). A swivel joint (80) connects the mouthpiece (40) to the mixing section (30). The mixing section (20) has a cover (290) which may be a transparent magnifying lens.

Arrow (460) shows the direction of air flow through the air passage (50) through the dry powder inhaler (10).

Figure 2:
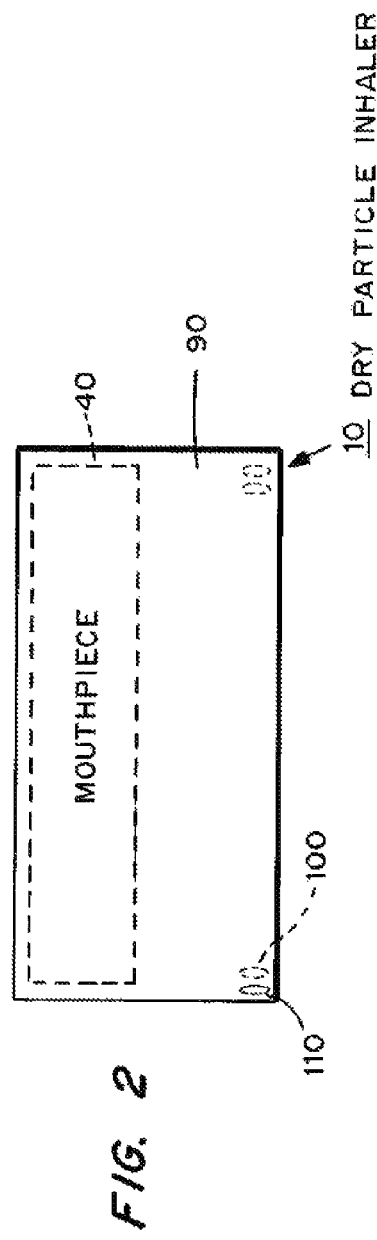
FIG. 2 is schematic view of the mouthpiece cover.

FIG. 2 shows the mouthpiece cover (90) in the closed position over the dry particle inhaler (10). Protrusions (100) on the mouthpiece cover (90) mate with grooves or depressions (110) on the dry particle inhaler (10), to join the mouthpiece cover (90) to the dry particle inhaler (10).

Figure 3:
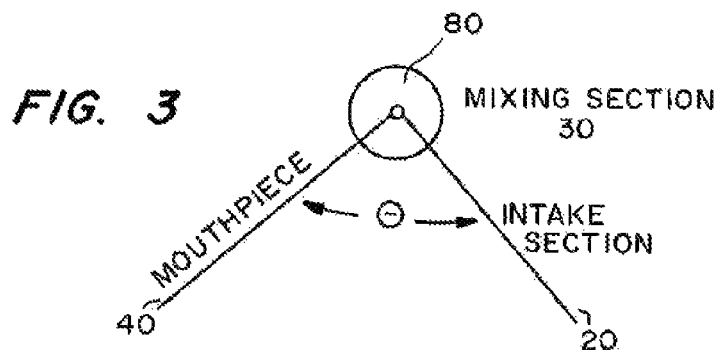
FIG. 3 is schematic view showing the angle between the intake section and the mouthpiece.

FIG. 3 is a schematic of the showing the mouthpiece (40) and the intake section (20) as represented by the longitudinal axis of the mouthpiece (70) and the longitudinal axis of the intake section (60). The swivel joint (80) connecting the mouthpiece (40) to the intake section (20) at the mixing section (30) may be regarded as the vertex of the angle. The importance of the angle (here called theta) between these two longitudinal axes will be further explained.

Figure 4:
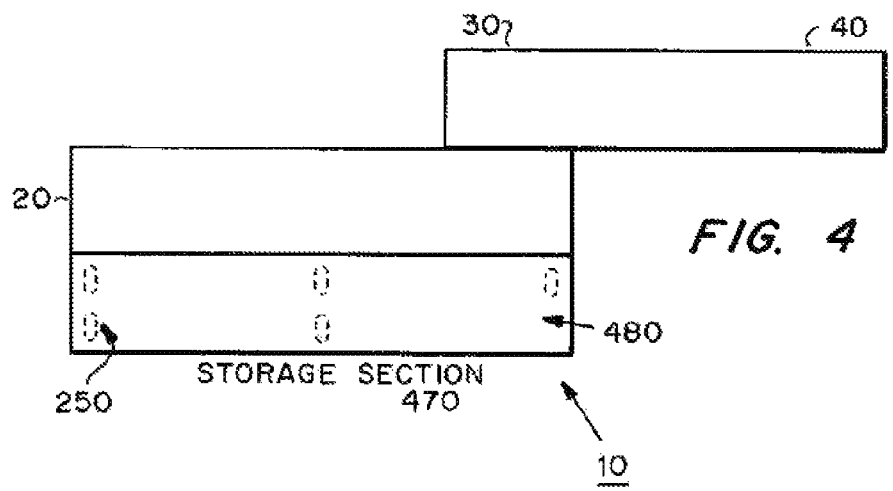
FIG. 4 is a schematic view of the dry particle inhaler, showing the storage section.

FIG. 4 shows the dry particle inhaler (10) with a storage section (470). Indicated as being inside the storage section (470) are mechanical fasteners (250) which operate to hold medicament capsules (300) (not shown in this Figure) in the storage section. In this embodiment, the storage section (470) is shown as appended to the intake section (20). The storage section has a cover (480) which may be a transparent magnifying lens, to allow the user to easily read writing on medicament capsules stored therein. The storage section cover (480) may swivel outward, or slide open on a track (not shown), or open by a variety of mechanisms known to those of skill in the art.

Figure 5:
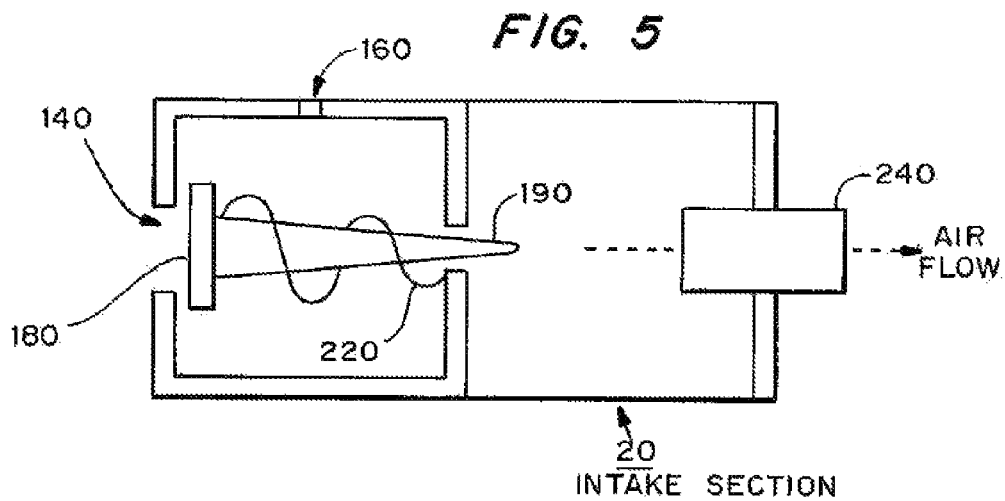
FIG. 5 is a schematic view of the intake section of the dry particle inhaler, showing the flow regulator and the feedback module.

FIG. 5 shows the intake section (20) of the dry particle inhaler (10). The direction of air flow is shown by the arrow (460). Air is admitted through an intake port (140) and one or more bleed orifices (160) [The bleed orifices may also be styled as secondary ambient air intake ports].

The piston (170) normally covers the intake port (140). When the user (not shown) inspires, the piston head (180) is drawn backwards, at a steady rate modulated by the spring (220). The spring (220) is fixed to the piston (170) and the inner wall (230) of the intake section chamber. Thus the rate of air flow is controlled. The air flow is further controlled by the tapering of the piston rod (190), past which the air flows. For further control of the air flow, a second spring (not shown) may also control the rate of movement of the piston (170).

The piston (170) and spring (220) combination allow the user (not shown) to generate a vacuum in his lungs before the intake port (140) opens.

Thus, by the time enough vacuum is generated to open the intake port (140), there will be sufficient air flow at a sufficient rate in the dry particle inhaler (10) to draw most of the medicament in the capsule (not shown) out of the inhaler into the proper place in the lungs of the user.

A feedback module (240) generates a signal to the user (not shown), which tells the user whether he is inspiring at the correct rate. The signal may be an audible one, in one embodiment a tone that is at a steady pitch when air flow is at a certain steady rate. In one embodiment of the dry particle inhaler (10), the signal is generated mechanically, such as be a musical reed. In another embodiment of the invention, the signal might be generated electronically, after electronic measurement of the air flow rate. The feedback module (240) would include a means for increasing or lessening the signal strength, or turning the signal off entirely. If the signal were generated by a reed, the mechanism for turning off the signal might be covering a bleed orifice which might admit the air flow generating the signal. If the signal were generated electronically, a simple push button or dial might turn on and off the signal.

Figure 6:
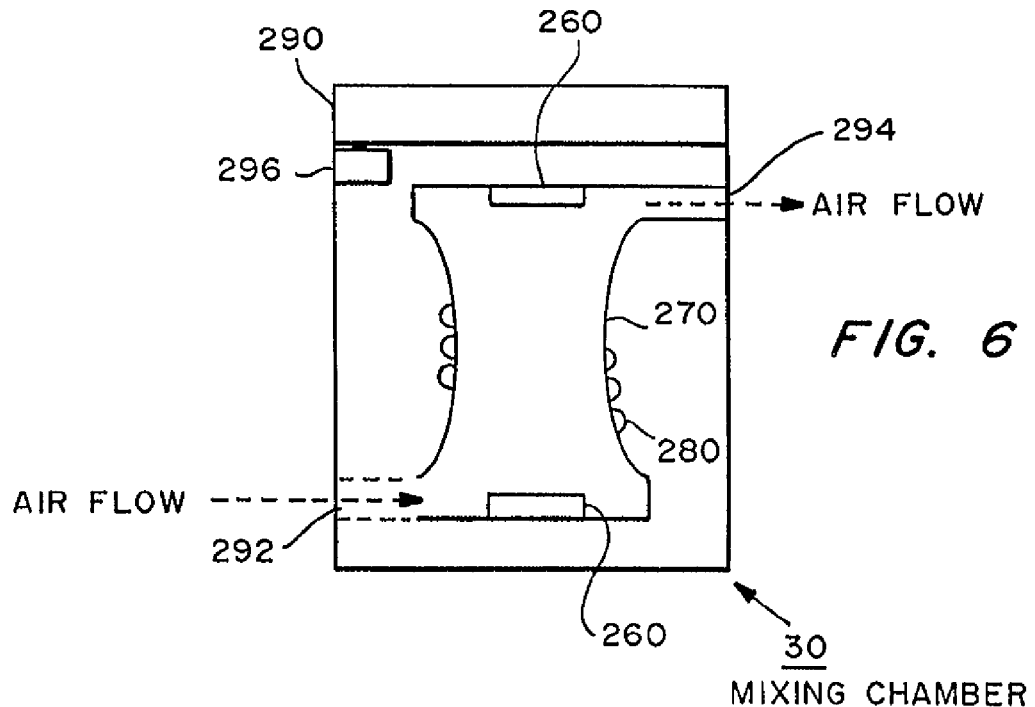
FIG. 6 is a schematic view of the mixing section.
Figure 7:
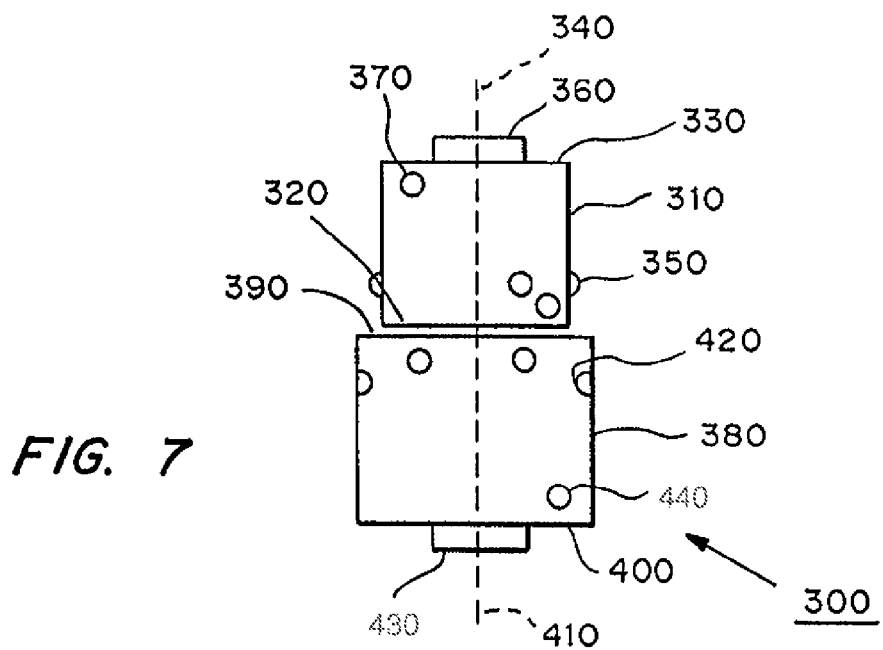
FIG. 7 is a schematic view of a capsule to hold medicament.

FIG. 6 shows a schematic of the mixing section (30) of the present invention. The mixing section has a cover (290), and a holder (260) for a medicament capsule (not shown). The holder (260) is a mechanism which grips and turns the capsule (not shown) to open and close it as the longitudinal axis (70) of the mouthpiece is rotated about the swivel joint (80) relative to the longitudinal axis (60) of the intake section. Such a mechanism may be straightforward: in a simplest embodiment, both the top and bottom halves (not shown) of the capsule could be fixed to their respective holders (260).

The Venturi chamber (270) speeds the flow of air near the capsule (not shown). Air flows in at (292), and out through (294). In one embodiment, air flows both through and around a capsule (not shown) holding a dry powder medicament. The special shape of the Venturi chamber (270), which further includes protrusions or spiral shapes (280), imparts a cyclonic flow to the air passing through the mixing section (30).

This helps to de-agglomerate particles of dry powder. The spiral shape of the interior of the mixing section (291) can be two separate spirals, in one embodiment of the invention. Mixing section (30) therefore provides the means whereby air flow is speeded up to suspend dry particles in air and de-agglomerate them, and then slow the air flow somewhat while the particles are still suspended in air. The cover (290) for the mixing section (30) may be a transparent magnifying lens, so that any writing on the capsule (not shown) may be read easily.

In one embodiment of the dry particle inhaler (10), the cover (290) of the mixing section may not be opened unless the longitudinal axis (70) of the mouthpiece forms a certain angle with the longitudinal axis (60) of the intake section, with the vertex of the angle being the swivel joint (80) connecting the mouthpiece (40) and the mixing section (30). The latch mechanism (296) for the cover (290) of the mixing section can accomplish this, by any of several mechanical means known to those of ordinary skill in the art. In the simplest embodiment, a catchment (not shown) in the cover (290) for the mixing chamber would be engaged by a slip ring (not shown) on the mixing section which was only a certain number of degrees of a circle.

When the mouthpiece (40) were rotated enough relative to the intake section (20), the slip ring (not shown) would no longer engage the catchment (not shown). In one embodiment, the user could open the cover (290) when the angle were between approximately ninety and one-hundred and eighty degrees.

FIG. 7 shows a medicament capsule (300) for use with an inhaler, be it a dry powder inhaler (10), or a liquid mist inhaler. The capsule (300) has two halves which fit together, here styled a first tube (310) and a second tube (380). Each tube has an open end (320,390), and a closed end (330,400). Each tube also has a long axis (340,410). In addition, each tube has a number of secondary holes (370,440). The first tube (310) fits inside the second tube (380) snugly. A protrusion (350) on the outer surface of the first tube (310) can slide past a corresponding protrusion (420) on the inner surface of the second tube (380). This locks the first tube (310) to the second tube (380). Therefore the first tube (310) and the second tube (380) have both an unlocked and a locked position. In the unlocked position, at least one secondary hole (370) in the first tube aligns with at least one secondary hole (440) in the second tube. This permits introduction of a medicament (not shown) into the capsule through the aligned secondary holes (370,440).

The first tube (310) may then be locked to the second tube (380). When a user (not shown) is ready to use a capsule (300), he simply places it in the holder (260) in the mixing section (30), and closes the cover (290). When the holder (260) rotates the first tube (310) around its long axis (340) relative to the second tube (380) and its long axis (410) (the axes are now coincident), that causes at least two secondary holes (370) in the first tube to align with at least two secondary holes (440) in the second tube. Air can now pass in, through, and out of the capsule (300), releasing the medicament contained therein. In one embodiment of the inhaler, the capsule (300) might open when the angle between the longitudinal axis (70) of the mouthpiece section, the vertex of the swivel joint (80), and the longitudinal axis (70) of the mouthpiece section were between one hundred and seventy and one-hundred and eighty degrees. This rotation of the mouthpiece (40) relative to the intake section (20) would cause a corresponding rotation of the first tube (310) about its long axis (340) relative to the second tube (380) and its long axis (410).

In one embodiment of the invention, several protrusions on the surfaces of the first tube or the second tube might provide a variety of locking positions. Similarly, a variety of secondary holes in the first and second tubes might provide a variety of rotational positions aligning or not aligning secondary holes on the first and second tubes.

The capsules described herein permit the introduction of liquid or gel medicament which can be dried in the capsule, creating a powder. This permits the accurate production of very small amounts of powdered medicament in a capsule, since it can be formed from a larger volume of accurately metered liquid or gel medicament. This permits very accurate microdosing. In addition, chemical reactions and drug mixtures may be made directly in the capsules described herein, then the resulting formulation dried.

In one embodiment of the capsule (300), one or more of the secondary holes (370,440) used to admit air to the capsule is oval-shaped (elliptical). In one embodiment of the invention, the ratio of the long axis of the ellipse to the shorter axis may be between 1:1 and 3:1, and may be 2:1.

This ratio may be called a vertical aspect ratio. In one embodiment of the invention, the intersection of the surface defining one or more of the secondary holes (370,440) and the surface defining the interior of the capsule (300) meet in a chamfered, or beveled, edge. This chamfered edge creates a vortex when air flows through the secondary holes (370,440).

Each capsule (300) also has a keying surface (or fastening mechanism) on the closed end (330) of the first tube and the closed end (400) of the second tube comprising the capsule. The keying surface (360) on the first tube may be different from the keying surface (430) on the second tube.

That permits easy tactile and visual identification of the orientation of the capsule. It also permits a system where each drug formulation in a capsule (300) corresponds to a dry particle inhaler (10), so users cannot mix up drugs. In one embodiment of the invention, the keying surface (360) of the first tube mates with a keying surface (430) of a different second tube, or the mechanical fasteners (250) of the storage section (470). This permits easy storage of the capsules (300) in the storage section (470).

FIG. 18 shows a medicament capsule (300), with a keying surface (360) on the first tube and a keying surface (430) on the second tube. It also shows a cutaway view of the mixing section (30) and the air flow entrance (292) to the mixing section and the air flow exit (294) to the mixing section.

A spiral shape (280) is given to the interior walls (298) of the mixing section, to impart a cyclonic flow to air passing through. The air flow entrance (292) and air flow exit (294) in this embodiment are tangential to the imaginary tube we might call the mixing section interior (291). That is to say, if a radius were drawn perpendicular to the long axis of the tube, and a tangent line were drawn to the circle perpendicular to the radius, the air flow would exit the mixing section along that tangent line. The tangential air flow exit (294) increases the velocity of the air flow, and thus helps disperse the medicament particles. As can be seen from FIG. 18, the mixing section interior (291) is sized to accommodate a medicament capsule (300). Keying mechanisms (360,430) are shaped to mate with holder (260) in the mixing section. Capsules according to the present invention may have a number of shapes, including ovoid and rectangular shapes. A variety of shapes of protrusions and slots may also be employed as keying surfaces. For instance, a keying surface might be a rectangular block, and a capsule holder might have a rectangular orifice. Alternatively, a keying surface might be triangular, hexagonal, Z-shaped, C-shaped, etc., and the holder would have the correspondingly shaped aperture.

FIG. 18 also shows one embodiment of the capsule (300) where a cone (375) is located in the interior of the first tube, and a cone (445) is located in the interior of the second tube. These cones (375,445) cause the air flow within the capsule to be cyclonic, aiding in mixing the medicament particles with the air. A cone is shown herein, but other cyclone-creating structures are contemplated by the present invention.

Figure 8:
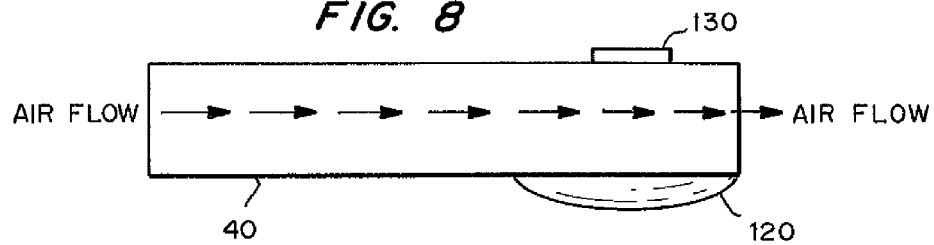
FIG. 8 is a schematic view of the mouthpiece.

FIG. 8 shows the mouthpiece (40) of the dry particle inhaler (10).

It has a protrusion (130) on its surface to contact the lips of a user (not shown). This helps the user place the mouthpiece correctly in his mouth.

The mouthpiece (40) also includes a tongue depressor (120), which may have a bulbous shape. The mouthpiece (40) is long enough that it fits approximately midway into the user's mouth (not shown). This permits greater delivery of medicament to the lungs, and less delivery to the oral cavity. The mouthpiece (40) has a particular aspect ratio of its inner channel (50) (see FIG. 17). This slows the air passing through the channel so that the air borne particulates do not end up striking the back of the user's throat.

However, the air is not slowed so much that the particulates settle out of the air flow.

Figure 9:
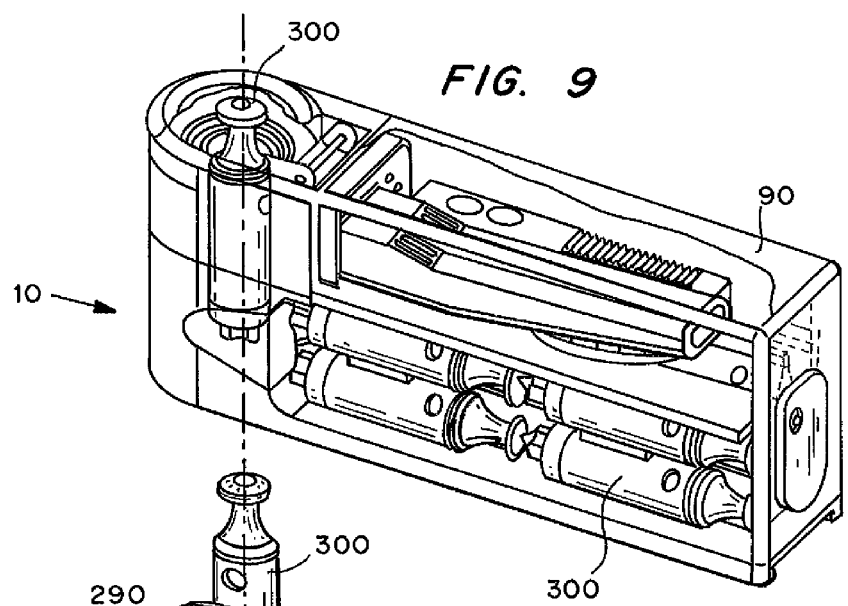
FIG. 9 is a perspective view of a specific embodiment of the dry particle inhaler in the closed position, with a capsule inserted into the mixing section, and extra capsules stored in the storage section.
Figure 10:
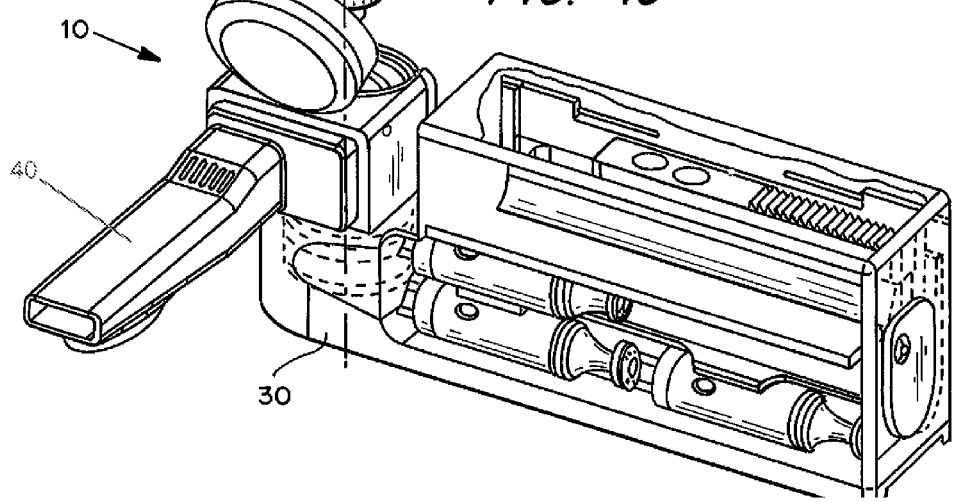
FIG. 10 is a perspective view of a specific embodiment of the dry particle inhaler showing a capsule being loaded in to the mixing section.
Figure 11:
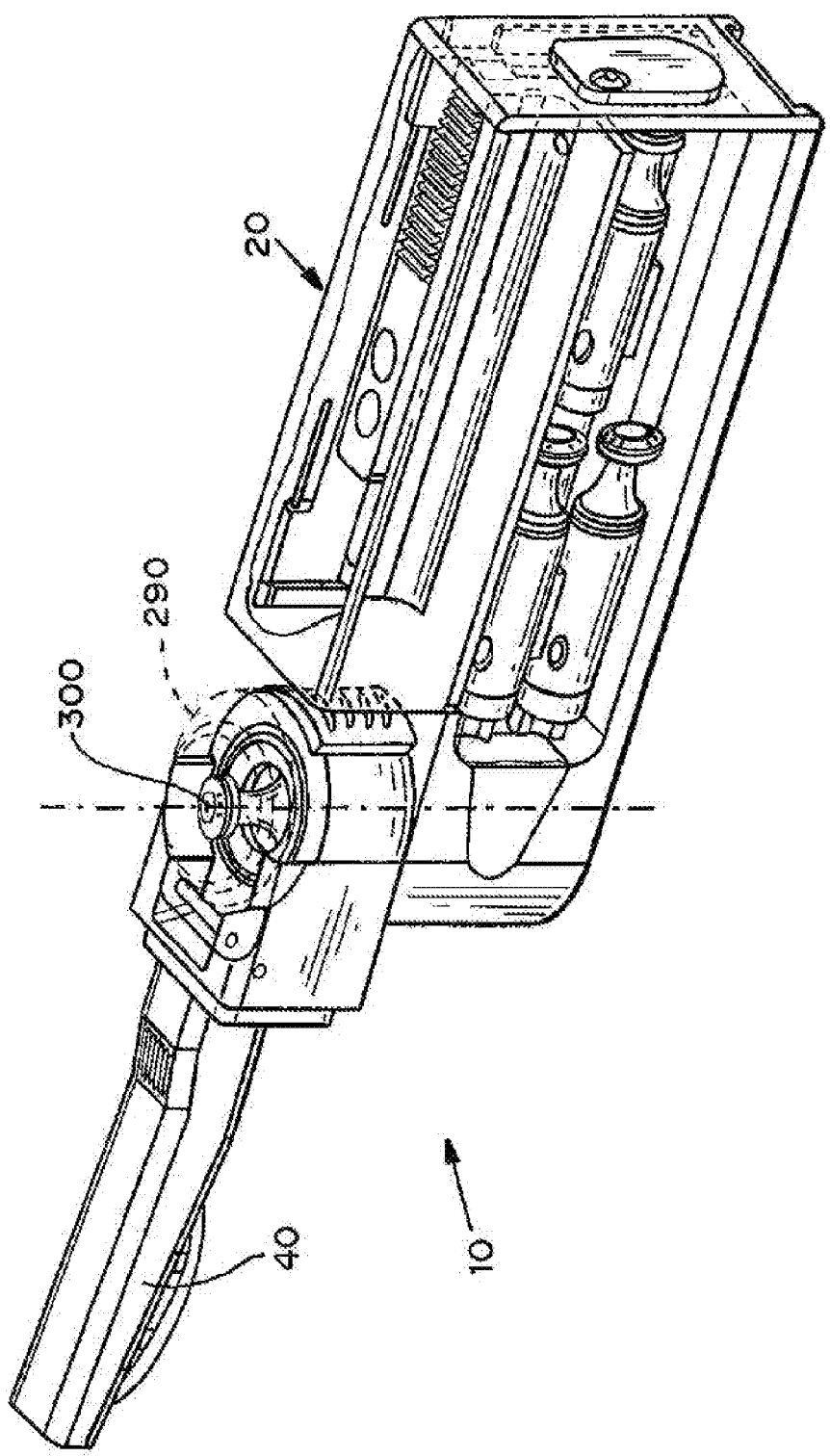
FIG. 11 is a perspective view of a specific embodiment of the dry particle inhaler showing a capsule inserted into the mixing section, and the mouthpiece extended for use.
Figure 14:
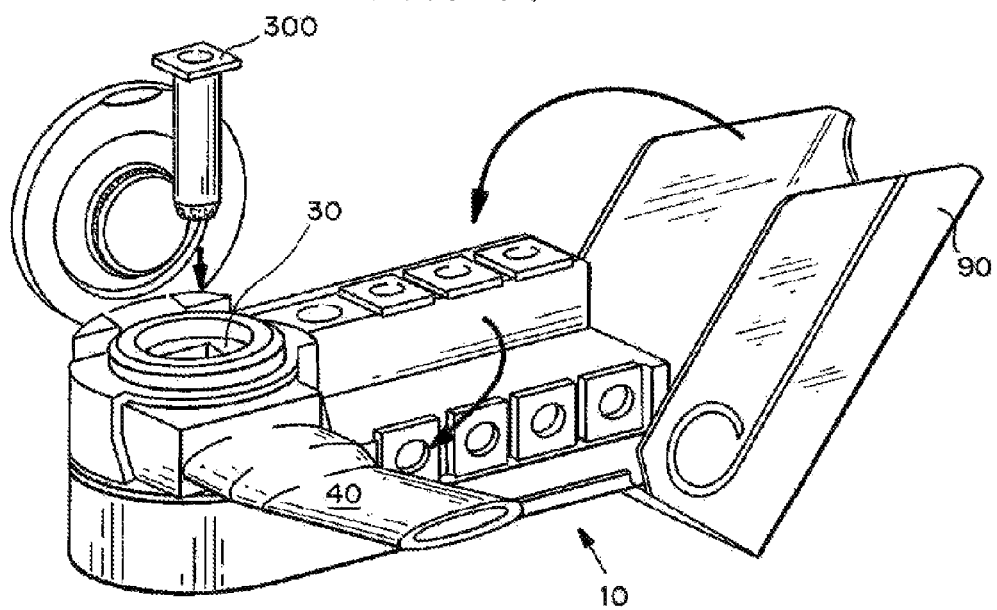
Figure 15:
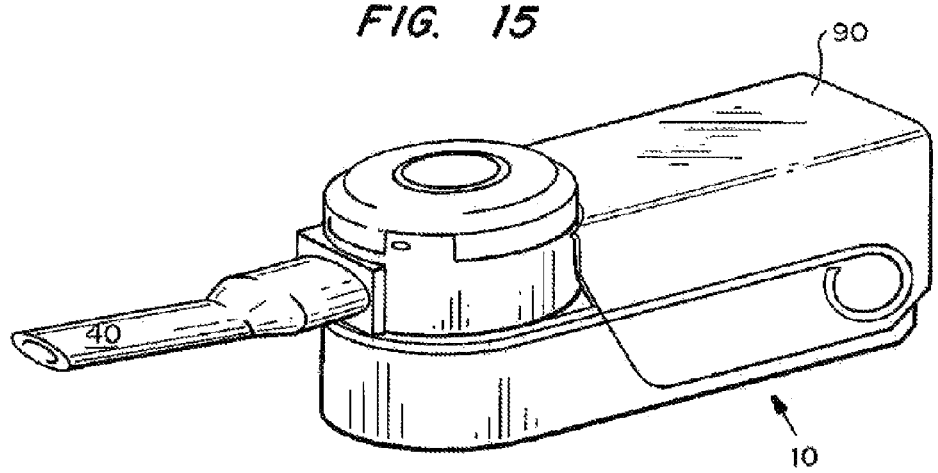

FIG. 9, FIG. 10, and FIG. 11 show one specific embodiment of the dry particle inhaler (10). In FIG. 9, the cover (90) of the mouthpiece is closed, and several capsule (300) are in the storage section (470). In FIG. 10, the mouthpiece (40) has been rotated relative to the intake section (20). The longitudinal axis (60) [not shown] of the intake section here makes an approximately ninety degree angle with the longitudinal axis (70) of the mouthpiece section. This permits the cover (290) for the mixing section to be opened. A medicament capsule (300) taken from the storage section (470) is about to be inserted into the mixing section (30). In FIG. 11, the mouthpiece (40) has been rotated to a fully extended position, the cover (290) for the mixing section has been closed, and the dry particle inhaler 910) is ready for use. In one embodiment of the dry particle inhaler (10), when the dry particle inhaler is in the closed position (FIG. 9), the interior of the intake section (20) would be isolated from the outside air, but the mouthpiece (40) interior and the mixing section interior (291) would not be, permitting them to dry out after being exposed to the humid breath of a user.

FIG. 12, FIG. 13, FIG. 14, and FIG. 15 show a temporal sequence where a capsule (300) of medicament is loaded into the mixing section (30) of a dry particle inhaler (10), and the mouthpiece (40) is extended for use. The dry particle inhaler (10) described herein can also be used for nasal delivery of medicaments. A small tube (not shown) can be fitted to the end of the mouthpiece (40), and the other end of the tube inserted into the nostril. Alternatively, the mouthpiece (40) may be replaced by a nosepiece (not shown), whose free end is sized to be inserted into a nostril of a user. In another embodiment, a device such as a bellows or a syringe is used to force air through the dry particle inhaler (10) into a nosepiece inserted into the nostril of a user (not shown).

Figure 16:
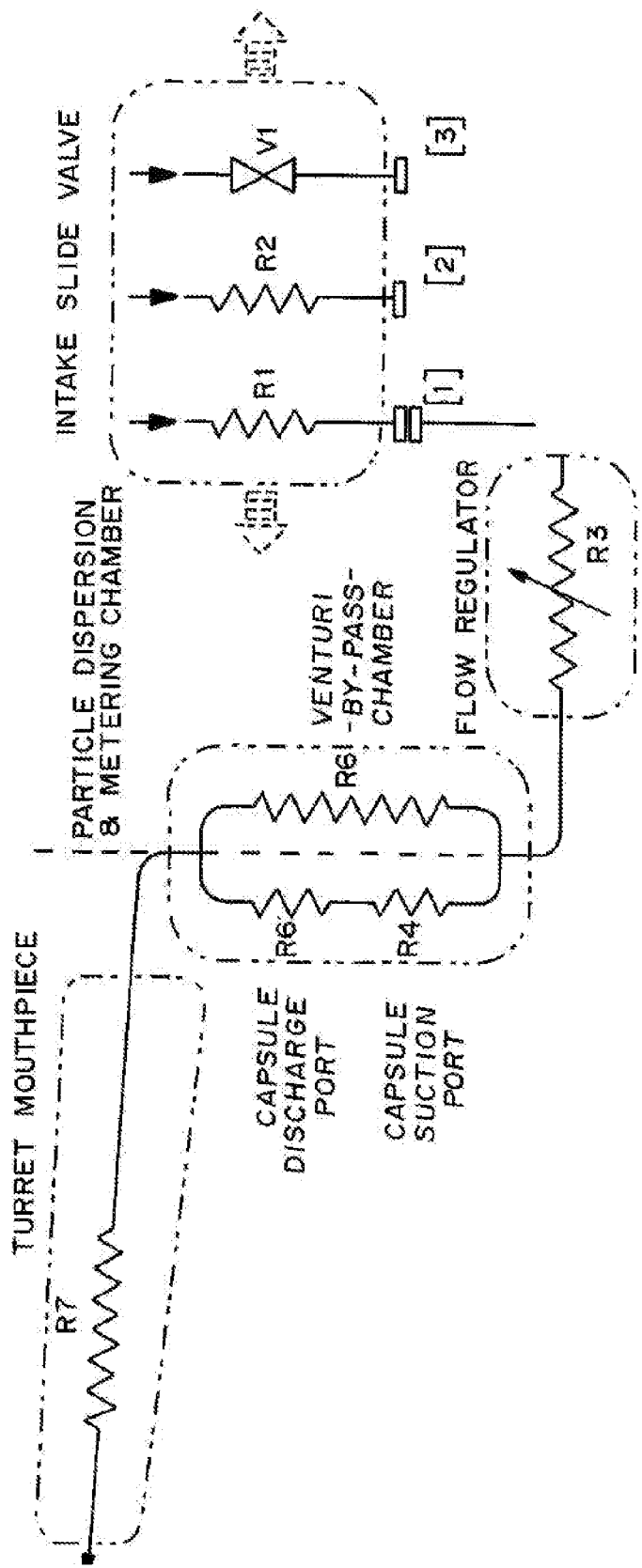
FIG. 16 is a view of a pneumatic circuit, where air flows (fluid flows) are represented by their electrical equivalents.

FIG. 16 shows the fluid (air) flow of the dry particle inhaler (10) modeled as the equivalent electrical circuit. This is styled a "pneumatic resistance circuit".

Figure 17:
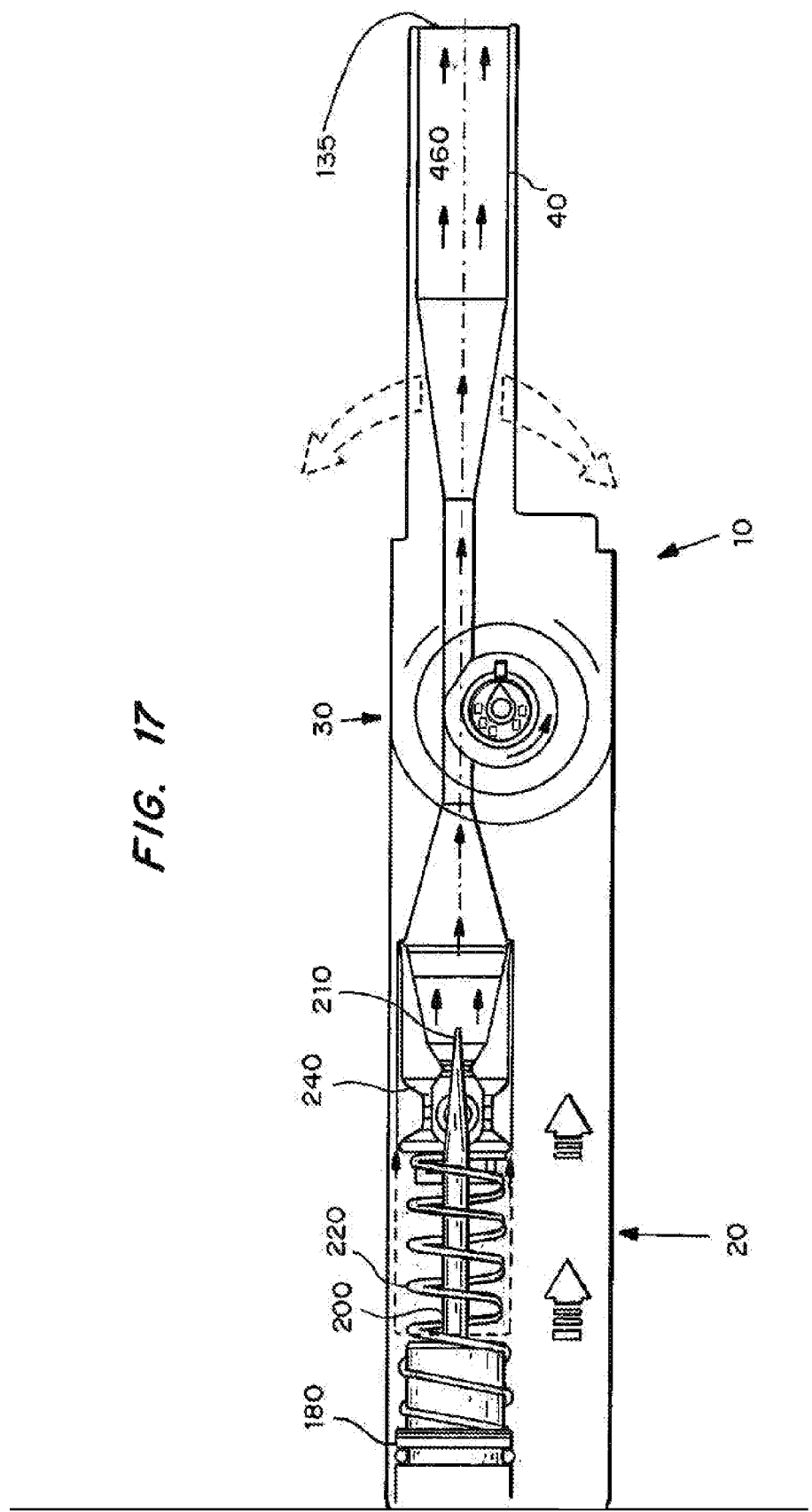
FIG. 17 is a schematic view of the dry particle inhaler.

FIG. 17 shows a schematic view of the dry particle inhaler (10). The air passage (50) through the dry particle inhaler widens as it goes through the mouthpiece (40) along the direction of the air flow (460). The opening (135) of the mouthpiece to be inserted into the mouth of the user may be roughly ellipsoid, or oval, and thus have a major axis and a minor axis. The ratio of these two may be called the horizontal aspect ratio. In one embodiment of the invention, the horizontal aspect ratio is between 2:1 and 4:1. In one embodiment of the dry particle inhaler (10), the horizontal aspect ratio is 3:1. Shaping the opening (135) in this manner keeps the drug particles collimated, maintains the optimal velocity of the particles in the air stream, and is oriented to the natural horizontal aspect ratio of the oropharyngeal region of the mouth. In one embodiment of the invention, the outline of the opening (135) resembles a bean.

The dry particle inhaler described herein may be used with medicament particles of low, medium, and high shear forces.

The dry particle inhaler and capsules described herein may be made with a variety of suitable materials known to those skilled in the art, such as metal, glass, rubber, and plastic.

While the invention has been described with reference to particular embodiments, those skilled in the art will be able to make various modifications without departing from the spirit and scope thereof.

We claim:

1. A dry powder inhaler comprising:
   an intake section;
   a mixing section; and
   a mouthpiece portion;
   wherein the intake section and mouthpiece portion each have a longitudinal axis, and air flows through a passage extending from the intake section through the mixing section through the mouthpiece portion, and wherein the mouthpiece portion is structurally configured to engage with the intake section and the mouthpiece portion is movable relative to the intake section, and
   wherein the inhaler further comprises a joint engaging the mouthpiece portion to the intake section, wherein the mixing section is a chamber which comprises a holder for a capsule having a top keying portion, and the holder is nested inside the chamber, wherein the holder grips the bottom portion of the capsule, and the holder opens the capsule when an angle defined by the longitudinal axis of the intake section and the longitudinal axis of the mouthpiece portion and the joint vertex is a first fixed number of degrees and closes the capsule when the angle defined by the longitudinal axis of the intake section and the longitudinal axis of the mouthpiece and the joint vertex is a second fixed number of degrees.

2. The dry powder inhaler of claim 1, wherein the mixing section comprises a mixing chamber configured to receive a medicament capsule.

3. The dry powder inhaler of claim 1 further comprising a cover operably configured on the inhaler over the mixing section.

4. The dry powder inhaler of claim 3 wherein the cover only opens when the mouthpiece portion attains a predetermined position relative to the intake section to load or unload a medicament capsule.

5. The dry powder inhaler of claim 4, wherein the predetermined position is between approximately ninety degrees and one hundred and eighty degrees.

6. The dry powder inhaler of claim 1, wherein the mixing section comprises a capsule holder and a swivel joint.

7. The dry powder inhaler of claim 1, further comprising a mouthpiece storage section within the dry powder inhaler, wherein the storage section houses the mouthpiece portion in a closed position.

8. The dry powder inhaler of claim 1 wherein the intake section comprises an inner channel, said intake section further comprising:
    an intake port;
    a flow regulator; and
    a bleed orifice;
    wherein the intake port and the bleed orifice both admit air to the dry powder inhaler, the rate of admission of said air being controlled by both the flow regulator and the bleed orifice and wherein the flow regulator comprises:
    i) a piston comprising a piston head connected to a piston rod; and
    ii) one or more springs connected to the piston and the inner walls of an intake chamber, wherein the piston rod is wider at its proximal portion connected to the piston head and narrower at its distal portion, the piston head covers the intake port, the piston head moves away from the intake port to admit air to the intake port, and wherein movement of the piston head is modulated by the springs connecting the piston to the inner walls of the intake chamber.

9. The dry powder inhaler of claim 8 wherein the intake chamber further comprises a feedback module mechanically connected to the intake chamber and the feedback module generates a signal in response to the flow of air in the intake chamber.

10. The dry powder inhaler of claim 9, wherein the feedback module comprises signal generators selected from the group consisting of electronic apparatuses to generate audio signals and mechanical devices to generate audio signals.

11. The dry powder inhaler of claim 9 wherein the signal from the feedback module is varied by a user of the dry powder inhaler.

12. The dry powder inhaler of claim 1, wherein the first fixed number of degrees needed to open the capsule is between approximately ninety degrees and one hundred and eighty degrees, and the second fixed number of degrees to dose the capsule is between approximately ninety and zero degrees relative to the intake section longitudinal axis.

13. The dry powder inhaler of claim 1, wherein the mixing section is a chamber which comprises a holder adapted and configured to receive and hold a capsule having at least one keying portion.

14. The dry powder inhaler of claim 1 wherein the mixing chamber comprises a Venturi chamber that is shaped to give air passing through it a cyclonic flow.

15. The dry powder inhaler of claim 1, wherein the mouthpiece portion is sized to extend into the oral cavity of a user.

16. The dry powder inhaler of claim 15 wherein the mouthpiece portion further includes a tongue depressor.

17. The dry powder inhaler of claim 1 wherein the mouthpiece portion has an outer surface comprising a protrusion on the outer surface to contact the lips of the user and to indicate to the user that the dry powder inhaler is inserted into the oral cavity of the user in the correct position.

18. The dry powder inhaler of claim 1 wherein the mouthpiece portion has an inner channel shaped to enable a reduction in air velocity.

19. The dry powder inhaler of claim 1 wherein the mouthpiece has an air passage and an opening having a major axis and a minor axis, said opening having a horizontal aspect ratio between 2:1 and 4:1.

20. The dry powder inhaler of claim 1 wherein the inhaler comprises a pneumatic resistance circuit.

21. The dry powder inhaler of claim 1, wherein each of the intake section, mixing section and mouthpiece portion comprise an inner channel and wherein the inner channel of the intake section is isolated from outside air while the inner channel of the mixing section and the inner channel of the mouthpiece portion are exposed to outside air when the mouthpiece portion is in a capsule loading and unloading position.

22. The dry powder inhaler of claim 1, wherein the mixing section has a long axis, and wherein the air flowing through the mixing section to the mouthpiece portion exits the mixing section at a tangent to a circle described by a radius about the axis of the mixing section.

23. The dry powder inhaler of claim 1, wherein the mixing section and the mouthpiece portion move about the intake section between a storage position, a capsule loading and unloading position and an extended position.

24. The dry powder inhaler of claim 23 wherein said extended position is at a configuration wherein the mouthpiece and intake section are separated by approximately one hundred and eighty degrees.

25. A dry powder inhalation system, comprising: a dry powder inhaler; and a capsule containing a medicament;
    wherein the dry powder inhaler comprises an intake section; a mixing section, and a mouthpiece portion; the intake section, the mixing section and the mouthpiece portion have an air flow passage extending from the intake section through the mixing section and the mouthpiece portion, and the mixing section comprises a cover, a mixing chamber and a capsule holder;
    wherein the capsule comprises a top half having at least one aperture and a bottom half having one or more additional apertures; and the bottom half is fitted into the top half and each of the top or bottom half has a key configured to engage with the dry powder inhaler; and
    wherein the mouthpiece portion is configured to engage and rotate about a swivel joint relative to the intake section.

26. The dry powder inhaler system of claim 25, wherein the capsule holder is configured to grip and turn the top half of the capsule about the bottom half of the capsule from a closed position to an open position of the capsule or from an open to a dosed position of the capsule when the mouthpiece portion is rotated.

27. The dry powder inhaler system of claim 26, wherein the apertures of the top half of the capsule align with at least one additional aperture of the bottom half of the capsule in the open position.

28. The dry powder inhaler system of claim 25, wherein the intake section comprises an intake chamber having an inner channel, one or more intake ports, a piston, at least one spring, and an exit port.

* * * * *

UNITED STATES PATENT AND TRADEMARK OFFICE
CERTIFICATE OF CORRECTION

| | | |
|---|---|---|
| PATENT NO. | : 8,146,588 B2 | Page 1 of 1 |
| APPLICATION NO. | : 11/949707 | |
| DATED | : April 3, 2012 | |
| INVENTOR(S) | : Steiner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1007 days.

Signed and Sealed this
Twelfth Day of June, 2012

David J. Kappos
*Director of the United States Patent and Trademark Office*